(12) United States Patent
Oyama et al.

(10) Patent No.: US 9,782,081 B2
(45) Date of Patent: Oct. 10, 2017

(54) PHOTOACOUSTIC APPARATUS

(71) Applicant: CANON KABUSHIKI KAISHA, Tokyo (JP)

(72) Inventors: Kenji Oyama, Tokyo (JP); Kazuhito Oka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 339 days.

(21) Appl. No.: 14/710,012

(22) Filed: May 12, 2015

(65) Prior Publication Data

US 2015/0327768 A1 Nov. 19, 2015

(30) Foreign Application Priority Data

May 14, 2014 (JP) ................. 2014-100849

(51) Int. Cl.
*A61B 5/00* (2006.01)

(52) U.S. Cl.
CPC .......... *A61B 5/0095* (2013.01); *A61B 5/4312* (2013.01); *A61B 5/708* (2013.01); *A61B 5/748* (2013.01); *A61B 2560/0475* (2013.01); *A61B 2562/046* (2013.01)

(58) Field of Classification Search
CPC ..... A61B 5/0095; A61B 5/748; A61B 5/4312; A61B 2562/046
See application file for complete search history.

(56) References Cited

U.S. PATENT DOCUMENTS

2013/0116536 A1 5/2013 Sato
2014/0093150 A1 4/2014 Zalev

FOREIGN PATENT DOCUMENTS

JP 2012-179348 A 9/2012
WO 2013082586 A2 6/2013

*Primary Examiner* — Joseph M Santos Rodriguez
(74) *Attorney, Agent, or Firm* — Canon USA, Inc., IP Division

(57) ABSTRACT

A photoacoustic apparatus disclosed herein includes a plurality of receiving elements which receive photoacoustic waves caused by irradiation of light from a light source to a subject and outputs reception signals and a signal data acquisition unit which generates and stores reception signal data by reducing a data amount of reception signals output from the plurality of receiving elements when a region where the directional axes of the plurality of receiving elements are gathered at a point is not included in a region of interest.

20 Claims, 5 Drawing Sheets

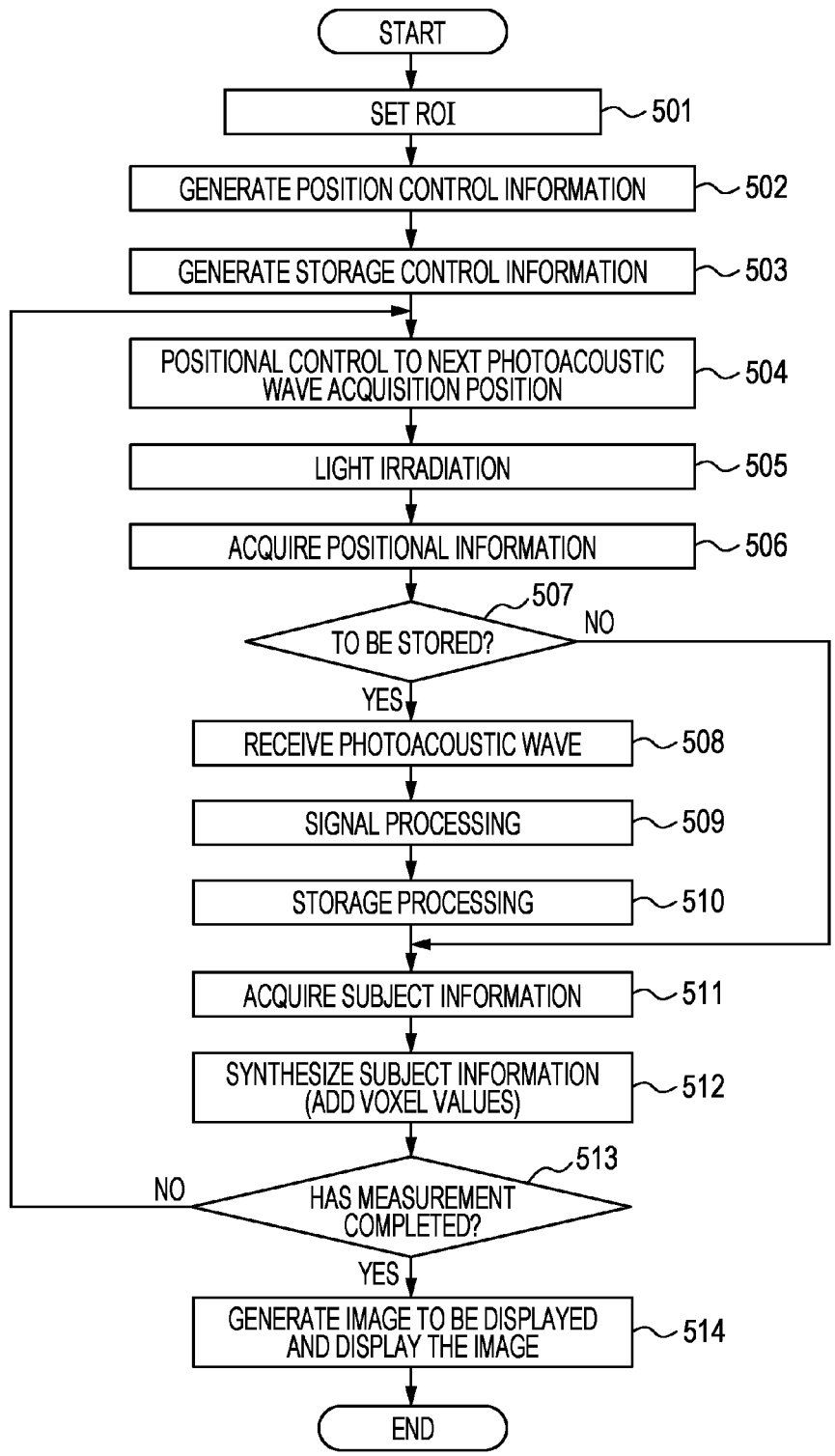

PHOTOACOUSTIC APPARATUS

BACKGROUND OF THE INVENTION

Field of the Invention

The present invention relates to a photoacoustic apparatus which uses a photoacoustic effect to acquire information on a subject (hereinafter, called subject information).

Description of the Related Art

A technology (Photo Acoustic Tomography or PAT hereinafter) which acquires functional information on a living body using light and ultrasound has been proposed in the past.

When a tissue of a living body is irradiated with pulsed light such as visible light and near-infrared light, a light absorbing substance, particularly a substance such as hemoglobin within blood within the living body absorbs energy of the pulsed light and instantaneously expands. As a result, photoacoustic waves (typically ultrasound) are generated. This phenomenon is called a photoacoustic effect, and PAT visualizes information of the biological tissue by measuring the photoacoustic waves. Visualizing a light energy absorption density distribution (density distribution of a light absorbing material within a living body which is a source of photoacoustic waves) as information of a biological tissue allows imaging of an active neovessel due to a cancer tissue. A light wavelength dependency of the occurring photoacoustic waves may be utilized to acquire functional information such as an oxygen saturation of blood.

The PAT technology allows non-exposure and non-invasive diagnostic imaging because it uses light and ultrasound for imaging biological information and achieves a large advantage in view of burdens on a patient. Therefore, use of the technology is expected for screening of a breast cancer and an early diagnosis, instead of an X-ray apparatus which is difficult to be used for repetitive diagnoses.

Japanese Patent Laid-Open No. 2012-179348 discloses a technology which acquires wide-range subject information by mechanically scanning a probe including a plurality of acoustic wave receiving elements arranged at different positions on a hemispherical surface. The direction of reception of the acoustic wave receiving elements arranged on the spherical surface are caused to point to a predetermined region to visualize the predetermined region with a high resolution. The position of the hemispherically shaped probe, that is, a predetermined region which may be visualized with a high resolution, may be mechanically scanned so that a wide range subject region may be visualized all over with a high resolution.

The apparatus disclosed in Japanese Patent Laid-Open No. 2012-179348 requires storage of a reception signal output from a transducer in a memory when probes are positioned at a plurality of positions. On the other hand, reduction of the amount of data of a reception signal to be stored in memory has been demanded.

SUMMARY OF THE INVENTION

A photoacoustic apparatus disclosed herein includes a plurality of receiving elements which receive photoacoustic waves caused by irradiation of light from a light source to a subject and outputs reception signals and a signal data acquisition unit which generates and stores reception signal data by reducing a data amount of reception signals output from the plurality of receiving elements when a region where the directional axes of the plurality of receiving elements are gathered at a point is not included in a region of interest region of interest.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIG. 5 is a flow chart illustrating a flow for acquisition of subject information according to an embodiment.

DESCRIPTION OF THE EMBODIMENTS

Figure 1:
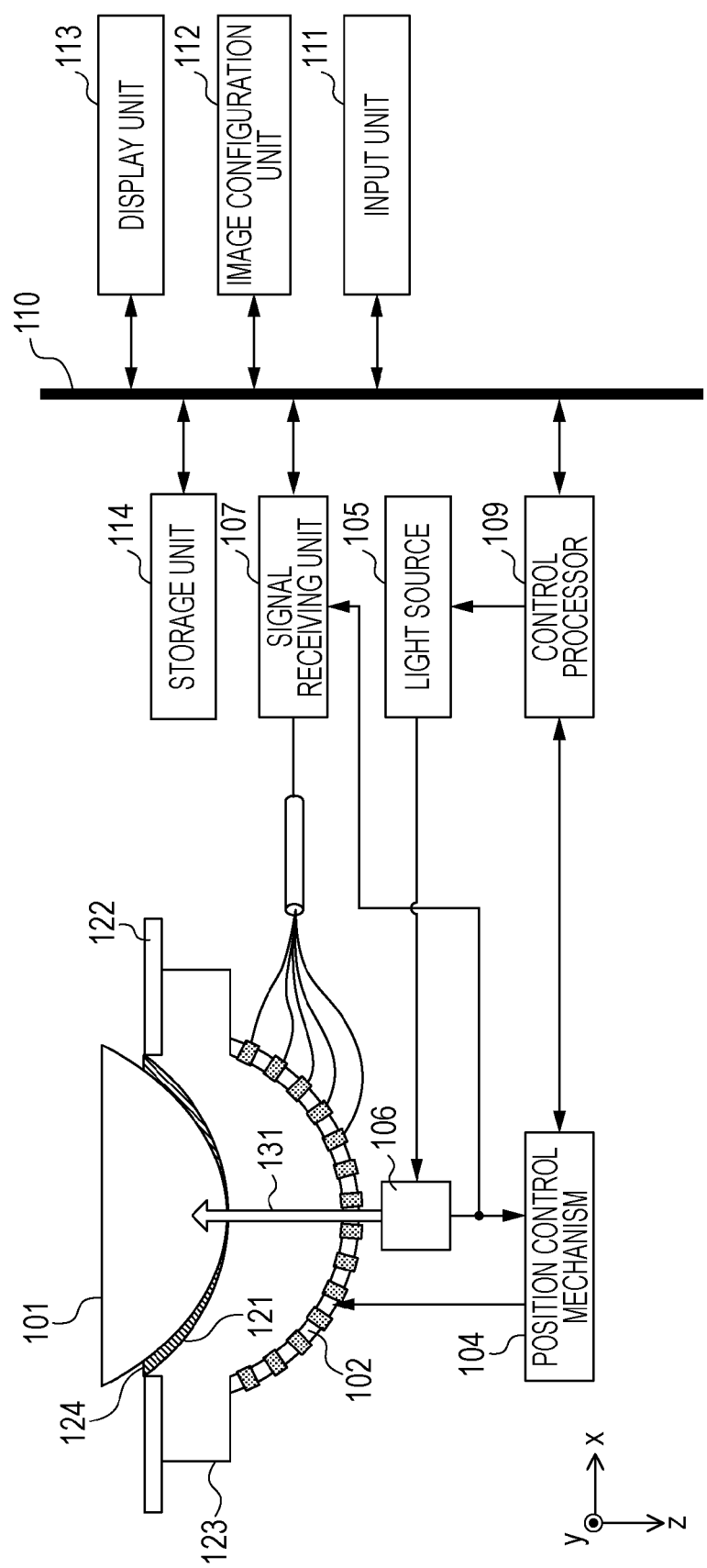
FIG. 1 is a schematic view of an apparatus configuration of a photoacoustic apparatus according to an embodiment.

The term "acoustic wave" herein typically refers to an ultrasonic wave and includes an elastic wave called a sonic wave, an ultrasonic wave, or an acoustic wave. For convenience of description, an elastic wave occurring within a subject when the inside of the subject is irradiated with light, such as a near-infrared ray, will be called a photoacoustic wave.

A photoacoustic apparatus of the present invention uses a reception signal of a photoacoustic wave to acquire subject information describing values corresponding to a plurality of positions within a subject. The subject information acquired with a photoacoustic wave reflects an absorptivity of light energy. More specifically, such subject information acquired by a photoacoustic apparatus may be information reflecting an initial sound pressure of occurring photoacoustic waves, a light energy absorption density and an absorption factor derived from the initial sound pressure, and a concentration of a substance included in a tissue. A concentration of a substance may refer to an oxygen saturation, a total hemoglobin concentration, an oxyhemoglobin or a deoxyhemoglobin concentration, for example. The subject information at a plurality of positions may be acquired as a two-dimensional or three-dimensional distribution. A distribution of such subject information may be generated as image data describing subject information regarding the inside of a subject.

A photoacoustic apparatus according to an embodiment will be described which includes a probe having a plurality of acoustic wave receiving elements such that their axes (each called a directional axis) are provided along a direction with a highest receiving sensitivity. In other words, the probe has a plurality of acoustic wave receiving elements arranged such that acoustic waves occurring in a predetermined region having the directional axes may be received with high sensitivity. In the photoacoustic apparatus according to this embodiment, relative positions of the probe and a subject are changed, and the probe receives a number of acoustic waves over time. Time-series reception signals output from the probe are stored in memory as reception signal data. The photoacoustic apparatus according to this embodiment uses the reception signal data stored in memory over a plurality of times to acquire subject information regarding each target position within a region of interest region of interest.

In a case where subject information is acquired by using reception signals acquired by receiving acoustic waves with the probe according to this embodiment at a certain position, a highest resolution may be achieved at a predetermined position where directional axes of a plurality of acoustic wave receiving elements are typically gathered to a point (i.e. where the directional axes meet, or a focused). As the distance from the predetermined position increases, the resolution for subject information decreases. In this case, it may be estimated that acoustic waves occurring in a predetermined region having half the resolution of the highest resolution at the predetermined position may be received by the probe with a higher sensitivity. In the description of this embodiment, a region with half the resolution of a highest resolution at a predetermined position will be called a "high sensitivity region". For example, in a case of a probe in which a plurality of acoustic wave receiving elements are supported by a hemispherical base material, the predetermined position where directional axes are gathered most (i.e. where the directional axes are gathered at a point or focus) corresponds to the center of a curvature of the hemispherical base material.

A moving region of a probe may sometimes be set based on measurement condition such as a force (acceleration) occurring along with a movement of a probe to be applied to components of the probe, a total moving time period, or a time for restraining a subject. Alternatively, moving regions of several predetermined probes to be applied as the apparatus may sometimes be set in advance.

However, in a case where a predetermined position where directional axes are gathered most, or a high sensitivity region, does not fit within a region of interest region of interest, it is difficult for acoustic wave receiving elements arranged in the probe to receive with high sensitivity photoacoustic waves occurring within the region of interest region of interest. In other words, reception signals output from the acoustic wave receiving element in this case are reception signals which do not largely contribute to the highly accurate acquisition of subject information regarding the inside of the region of interest region of interest. Therefore, storage of such reception signals may enlarge the amount of stored data and thus increase the memory capacity. The storage of such reception signals may increase the times for subsequent data processing, data communication, and acquisition of subject information.

This embodiment reduces the data amount of reception signals which are output from the acoustic wave receiving elements provided in the probe when a predetermined position where directional axes are gathered most is not included in a region of interest region of interest. Furthermore, this embodiment may reduce the data amount of reception signals which are output from the acoustic wave receiving elements provided in the probe when the high sensitivity region is not included in the region of interest region of interest. In order to reduce the data amount, target reception signals may not be stored, or the sampling frequency for target reception signals may be lowered than the sampling frequency for the other reception signals, for example. Any approach may be used as far as it allows reduction of the data amount of target reception signals.

This photoacoustic apparatus allows selective reduction of the data amount of reception signals which do not largely contribute to highly accurate acquisition of subject information. Thus, both highly accurate acquisition of subject information within a region of interest region of interest and reduction of the memory capacity may be achieved.

A region of interest region of interest and a moving region of a probe are preset such that a predetermined position where directional axes are gathered most may fit within the region of interest region of interest. In this case, all reception signals output from a probe at different positions may not easily include a reception signal which does not largely contribute to highly accurate acquisition of subject information regarding the inside of the region of interest region of interest. On the other hand, when a region of interest region of interest or a probe moving region is set with some degree of freedom, there is an increased possibility that a predetermined position where directional axes are gathered most does not fit within the region of interest region of interest. Particularly, in a case where a region of interest or a probe moving region is changeable and is not included in the region of interest, the data amount of reception signals output from acoustic wave receiving elements provided in the probe may be reduced.

First Embodiment

A first embodiment will be described with reference to drawings.

Description of Components

FIG. 1 is a schematic view of a configuration of a photoacoustic apparatus according to a first embodiment.

The photoacoustic apparatus according to this embodiment includes a probe 102, a position control mechanism 104, a light source 105, an irradiation optical system 106, a signal receiving unit 107, a control processor 109, a system bus 110, an input unit 111, an image configuration unit 112, a display unit 113, and a storage unit 114.

Subject 101

A subject 101 is to be measured. Concrete examples thereof may be a living body such as a breast and a phantom simulating an acoustic property and an optical property of a living body for apparatus adjustment. The acoustic property specifically refers to a propagation velocity and attenuation rate of acoustic waves, and the optical property specifically includes a light absorption factor and a scatter factor. A light absorbent within a living body as a subject may be hemoglobin, water, melanin, collagen, or lipid, for example. In a phantom as described above, a substance simulating an optical property is enclosed within the light absorbent.

According to this embodiment, the subject 101 is held within a retaining unit 121 configured to retain a shape of the subject 101. The retaining unit 121 is attached to an attachment unit 122. The attachment unit 122 is configured to accept the retaining unit 121 having various shapes, and the retaining unit 121 adapted to the subject 101 may be attached thereto. In other words, a plurality of retaining units 121 may be provided, where each of the plurality of retaining units 121 has a different shape such that each of the retaining units 121 is capable of holding the shape of a differently shaped subject 101. Thus, a plurality of differently shaped subjects 101 can be accommodated by selection of an appropriately shaped retaining unit 121 from a plurality retaining units 121.

Probe 102

Figure 2A:
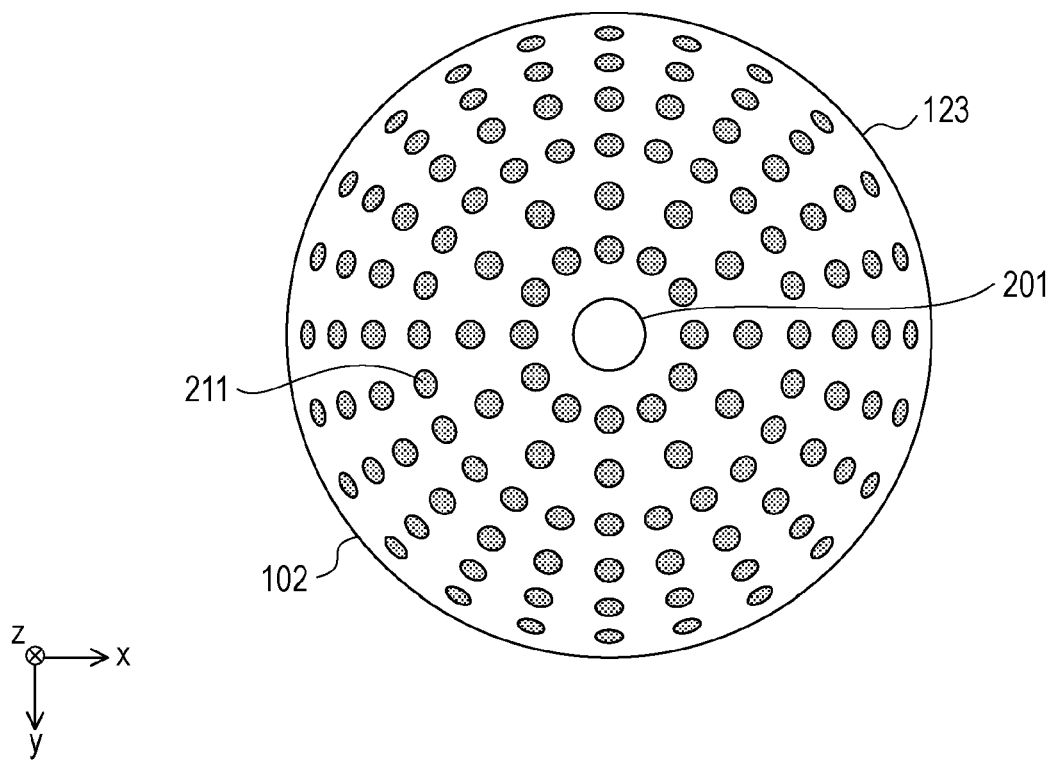
FIGS. 2A and 2B are conceptual diagrams illustrating a configuration of probes according to an embodiment.
Figure 2B:
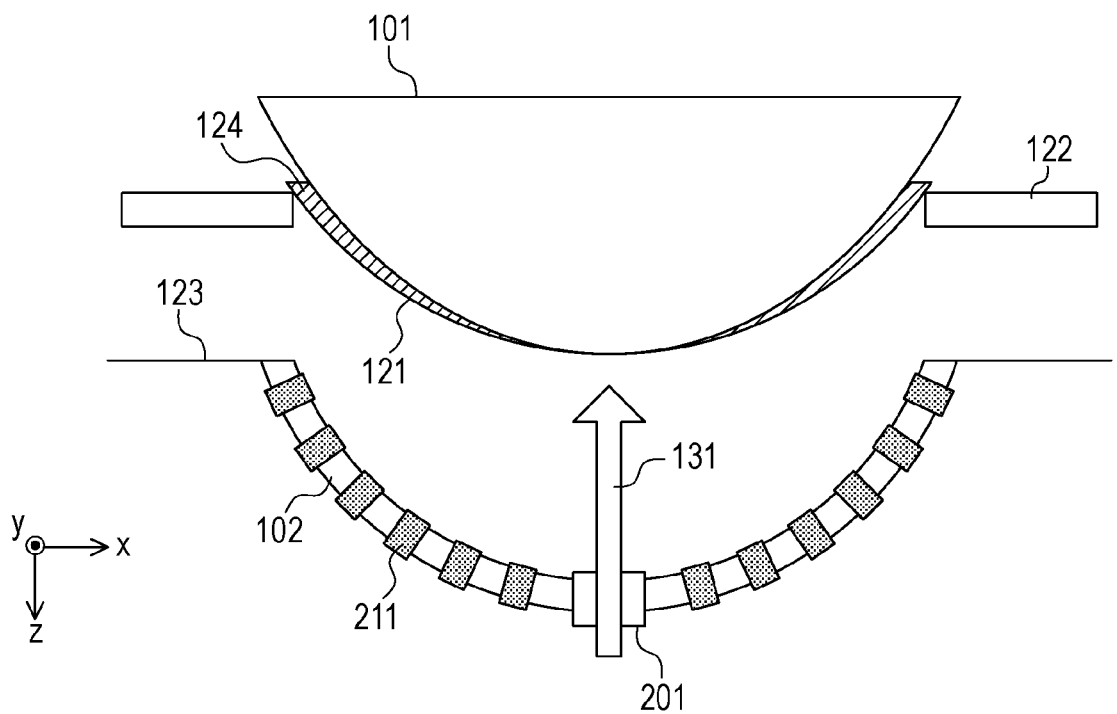

The probe 102 includes a base material 123 and a plurality of acoustic wave receiving elements 211 (see e.g. FIGS. 2A and 2B). The base material 123 supports the plurality of acoustic wave receiving elements 211 such that directional axes of the plurality of acoustic wave receiving elements 211 are gathered (i.e. the directional axes are gathered at a point or focus). In other words the directional axes of the plurality of acoustic wave receiving elements meet at a point (or focus). According to this embodiment, as illustrated in FIGS. 2A and 2B, the base material 123 is hemispherical, and the plurality of acoustic wave receiving elements 211 are disposed at different positions along the hemispheric shape. FIG. 2A is a top view of the probe 102 in a z-axis direction, and FIG. 2B is a side view of the probe 102 in a y-axis direction.

The acoustic wave receiving elements 211 receive photoacoustic waves occurring inside of the subject 101 when the subject is irradiated with light 131, convert them to electric signals and output them as reception signals. According to this embodiment, any suitable type of acoustic wave receiving elements may be used. For example, acoustic wave receiving elements using piezoelectric ceramics (PZT) may be used which are used in general ultrasonic diagnosis apparatuses. Alternatively, capacitive CMUT (or Capacitive Micromachined Ultrasonic Transducer), MMUT using a magnetic film (Magnetic MUT), or a PMUT using a piezoelectric thin film (Piezoelectric MUT) may be used.

Figure 3A:
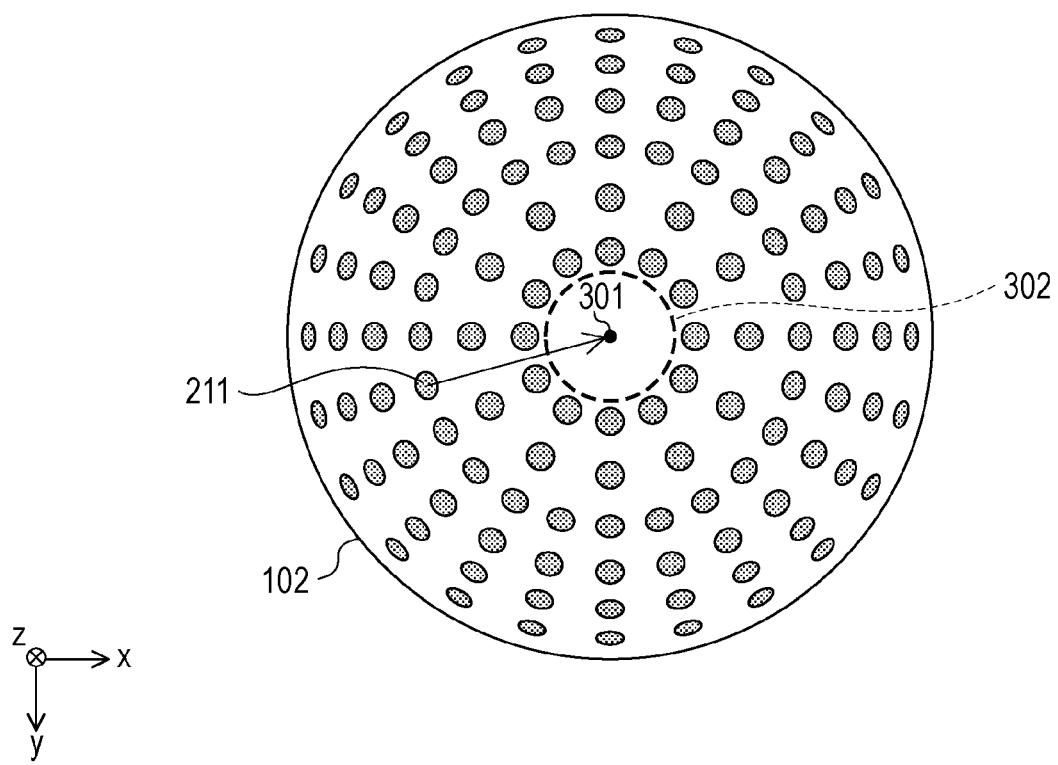
FIGS. 3A and 3B are conceptual diagrams illustrating a reception characteristic of probes according to an embodiment.
Figure 3B:
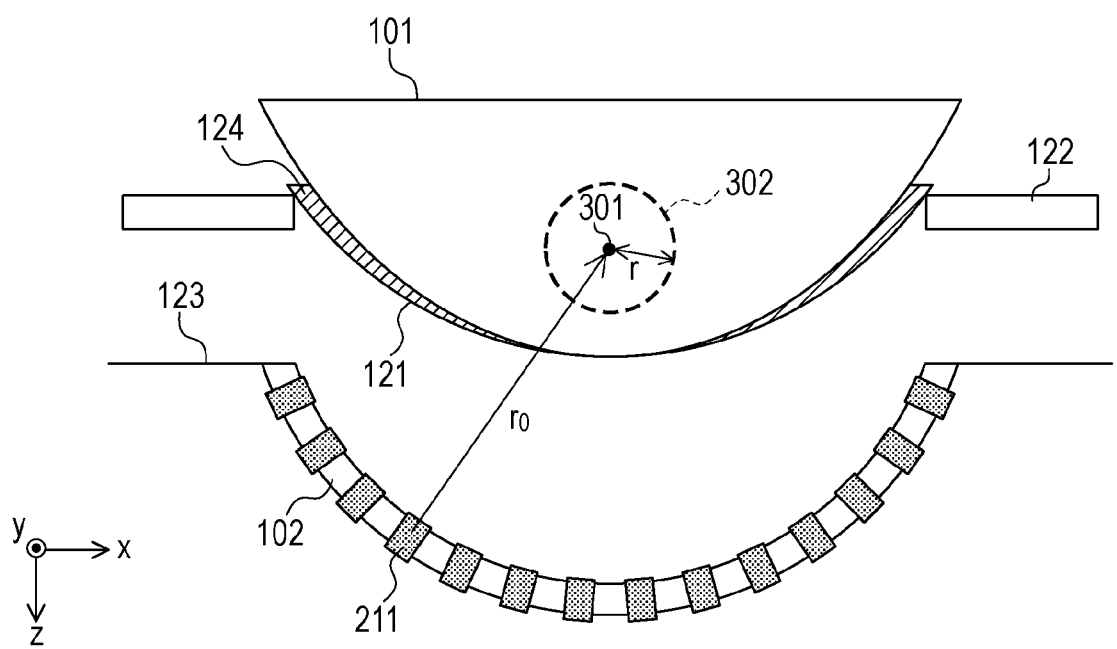

With reference to FIGS. 3A and 3B, a reception characteristic of the probe 102 will be described. FIG. 3A is a top view of the probe 102 in the z-axis direction, and FIG. 3B is a side view of the probe 102 in the y-axis direction, like FIGS. 2A and 2B.

For example, the plurality of acoustic wave receiving elements 211 included in the probe 102 are disposed along the hemispheric shape as illustrated in FIGS. 2A and 2B. A point 301 indicates a curvature center point of the hemispherical base material 123.

Generally, each of the plurality of acoustic wave receiving elements 211 has a highest receiving sensitivity in a normal line direction of its reception plane (surface). The directional axes of the plurality of acoustic wave receiving elements included in the probe 102 may be gathered near the curvature center point 301 of the hemispherical shape so that a region 302 which allows highly accurate visualization may be formed about the curvature center point 301. The region 302 corresponds to the high sensitivity region. By scanning the probe 102 by using the position control mechanism 104 or moving the region 302 about the subject 101, wide range subject information may be visualized with high accuracy.

For example, the high sensitivity region 302 may be considered as a substantially spherical region having a radius r expressed by the following Expression (1) about the curvature center for acquiring a highest resolution.

$$r = \frac{r_0}{\phi_d} \cdot R \quad (1)$$

In Expression (1), R is a lower limit resolution of the high sensitivity region 302, r0 is a radius of the hemispherical probe, and $\phi d$ is a diameter of the acoustic wave receiving element 211. R may be a half resolution of the highest resolution acquired at the curvature center, for example.

A case will be discussed in which the high sensitivity region 302 is substantially spherical about the curvature center point 301 of the probe 102. In this case, from the position of the probe 102 (or the curvature center point 301), the range of the high sensitivity region 302 at positions of two-dimensional scanning of the probe 102 may be deducted based on Expression (1).

According to the present invention, the layout of the plurality of acoustic wave receiving elements 211 is not limited to a hemispherical shape as illustrated in FIG. 2B or FIG. 3B. The plurality of acoustic wave receiving elements 211 may be arranged such that their directional axes may be gathered in a predetermined region to form a predetermined high sensitivity region. In other words, in order to form the predetermined high sensitivity region 302, a plurality of acoustic wave receiving elements may be arranged along a curved surface to form the predetermined region. The curved surface herein may include a spherical surface such as a spherical form or a hemispheric surface having an opening. The curved surface may further include a plane having a concave part and a convex part which may be regarded as a spherical surface and a plane on an ellipsoid which may be regarded as a spherical surface (three-dimensionally extended ellipse having a two-dimensional curved surface).

A curved surface based on a sphere includes the spherical surface or the plane which be regarded as the spherical surface. The hemispherical base material 123 according to this embodiment is also an example of such a base material having a curved surface based on a sphere.

The directional axes of the individual acoustic wave receiving elements do not necessarily cross one another as long as a desired high sensitivity region can be formed. It is sufficient that the directional axes of at least some of the plurality of acoustic wave receiving elements 211 converge in a specific region so that photoacoustic waves generated in the specific region can be received with high sensitivity. That is, it is sufficient that the plurality of acoustic wave receiving elements 211 are arranged so that at least some of the plurality of acoustic wave receiving elements 211 are able to receive photoacoustic waves generated in a high sensitivity region with high sensitivity.

The probe 102 further has an irradiation port 201 for guiding light 131 to its bottom face. The light guided to the irradiation optical system 106 is irradiated from the irradiation port 201 to the subject 101. An optical system according to the present invention may include the irradiation optical system 106 and the irradiation port 201. Position Control Mechanism 104

The position control mechanism 104 as a moving mechanism includes a driving unit such as a motor and a machine unit which transmits the driving force. The position control mechanism 104 moves the probe 102 about the subject 101 in accordance with position control information from the control processor 109 to move the irradiation position of the light 131 and the position for receiving photoacoustic waves. By repetitively acquiring reception signal data at the same time as moving the irradiation position of light 131 and the position for receiving photoacoustic waves about the subject 101, reception signal data for acquiring intended wide range subject information may be acquired.

The position control mechanism 104 outputs the positional information of the probe 102 when light is irradiated, that is, when photoacoustic waves are received to the control processor 109 in synchronism with one irradiation control of light 131 by the irradiation optical system 106.
Light Source 105

The light source 105 emits light for generating photoacoustic waves. For example, the light source 105 generates pulsed light having a center wavelength in a near-infrared band. The pulse width of the pulsed light may be 100 nsec or lower, but it is not limited to this value, any suitable pulse width may be used. The light source 105 generally is a solid-state laser (such as a Yttrium-Aluminum-Garnet laser and a Titan-Sapphire laser) capable of emitting pulsed light having a center wavelength in a near-infrared band. A laser such as a gas laser, a dye laser, and a semiconductor laser or light emitting diode instead of a laser may be used as the light source 105.

The wavelength of light is selected in accordance with a light absorbing material (such as oxyhemoglobin or deoxyhemoglobin, a malignant tumor mostly including a blood vessel or neovessel mostly including them, glucose or cholesterol) within a living body to be measured. For example, in a case where hemoglobin within a neovessel in a breast cancer is to be measured, light having wavelengths of 600 to 1000 nm is generally absorbed, and the light absorption relatively increases in wavelengths of 750 to 850 nm because the light absorption of water included in a living body is substantially minimum with around a wavelength of 830 nm. Because the light absorptivity depends on the light wavelength in some states (oxygen saturation) of hemoglobin, the wavelength dependency may be used to measure a functional change of a living body.

Irradiation Optical System 106

The irradiation optical system 106 guides pulsed light generated from the light source 105 to the subject 101 and forms and emits light 131 suitable for signal acquisition. The irradiation optical system 106 may typically include optical parts such as a lens and a prism for gathering or enlarging light, a mirror for reflecting light, and a diffuser for diffusing light. A light waveguide such as optical fiber may be used for a light guide from the light source 105 to the irradiation optical system 106.

As a standard relating to irradiation of a laser beam to the skin or eye, a maximum permissible exposure is provided in IEC60825-1 generally based on conditions such as light wavelengths, exposure duration times, and pulse repetitions. For the subject 101, the irradiation optical system 106 generates the light 131 which satisfies the standard.

The irradiation optical system 106 may include an optical configuration, not illustrated, which detects an emission of the light 131 to the subject 101 and generates a synchronism signal for controlling reception and storage of photoacoustic waves in synchronism with it. An emission of the light 131 may be detected by, for example, dividing a part of pulsed light generated by the light source 105 by using an optical system such as a half mirror, guiding the divided pulsed light to a light sensor, and using a detection signal generated by the light sensor. When a fiber bundle is used for guiding pulsed light, a part of the fibers may be diverged to guide light to a light sensor for detection. The synchronism signal generated by the detection is input to the signal receiving unit 107 and the position control mechanism 104.

Signal Receiving Unit 107

The signal receiving unit 107 converts a reception signal which is an analog electric signal output from the probe 102 to a digital reception signal. The signal receiving unit 107 outputs the generated digital reception signal to the storage unit 114, and the storage unit 114 stores the digital reception signal as reception signal data. According to this embodiment, the signal receiving unit 107 and storage unit 114 correspond to a signal data acquisition unit. Hereinafter, among electric signals acquired by receiving and outputting photoacoustic waves by acoustic wave receiving elements, a signal up to storage in a memory in a last stage of the signal data acquisition unit will be called a "reception signal", and signal data after storage in the memory in the last stage of the signal data acquisition unit will be called "reception signal data".

The signal receiving unit 107 may perform a process for correcting sensitivity variations between acoustic wave receiving elements in the probe 102 on the reception signals output from the probe 102 and a process for complementing a physically or electrically lost acoustic wave receiving element. The signal receiving unit 107 includes a signal amplification unit which amplifies an analog signal generated by the probe 102 and an A/D conversion unit which converts an analog signal to a digital signal.

Control Processor 109

The control processor 109 as a control unit causes an operating system (OS) to operate for controlling and managing a fundamental resource in a program operation. The control processor 109 further reads out a program code stored in the storage unit 114 and executes the following functions according to this embodiment. The control processor 109 manages an operation for acquiring subject information in response to an event notification caused by an operation for starting imaging from a user through the input unit 111, and controls hardware through the system bus 110. The control processor 109 further controls irradiation of light 131 required for generating target subject information, and controls the positions of the light 131 and probe 102. The control processor 109 controls storage of a reception signal based on a positional relationship between the position and a region of interest region of interest of the probe 102.

Input Unit 111

The input unit 111 receives an input from a user (mainly an examiner such as a medical staff) and sends input information to a component such as the control processor 109 through the system bus 110. For example, the input unit 111 may be used by a user to perform an image processing operation on an image such as instructing to set a parameter relating to imaging, and start imaging and setting an observation parameter such as a range and a shape of a region of interest region of interest. In general, the input unit 111 includes a mouse, a keyboard, and a touch panel and performs an event notification to software such as an OS operating on the control processor 109 in accordance with an operation performed by a user.

Image Configuration Unit 112

The image configuration unit 112 as an information acquisition unit acquires subject information at a target position within a region of interest based on reception signal data stored in the storage unit 114. In other words, the image configuration unit 112 converts reception signal data which is time-series data to subject information which is two-dimensional or three-dimensional spatial data. When a region of interest region of interest is a two-dimensional region, a target position is at a pixel. When a region of interest region of interest is a three-dimensional region, a target position is at a voxel.

The image configuration unit 112 generates a display image such as an arbitrary tomogram based on subject information at the acquired target position. The image configuration unit 112 applies correction processing such as brightness correction, and distortion correction, on the acquired subject information, and presentation of an identification of and extraction of a region of interest region of interest to generate a display image more suitable for a diagnosis. In response to a user operation through the input unit 111, a parameter to be used for acquiring subject information may be input, and a display image may be adjusted, for example.

Subject information at each target position may be acquired by performing an image reconstruction process on reception signal data stored in the storage unit 114, and subject information such as an optical property value distribution as described above may be visualized. The image reconstruction process may be a back projection or a phasing addition process in a time domain or a Fourier domain generally used in a tomography technology, for example. If it is not time critical, an image reconstruction scheme may be used such as inverse problem analysis performing repetitive processes. A probe having a reception focusing function with an acoustic lens may be used to visualize subject information without performing an image reconstruction process.

The image configuration unit 112 may include a GPU (Graphics Processing Unit) generally having high-performance calculation processing and graphics display functions. This may reduce the time for an image reconstruction process as described above and construction of a display image.

Display Unit 113

The display unit 113 displays a display image, of subject information generated by the image configuration unit 112 and a user interface (UI) for operating the image and the apparatus. The display unit 113 may be any type of display device such as a liquid crystal display and an organic electro luminescence (EL).

Storage Unit 114

The storage unit 114 may include a volatile or non-volatile memory for operating the control processor 109, and a volatile memory for temporarily holding data during the operation for acquiring subject information. The storage unit 114 may include a non-volatile, computer readable storage medium such as a hard disk which stores and holds generated reception signal data, subject information, and related diagnosis information. A non-volatile, computer readable storage medium as the storage unit 114 stores a software program code for implementing a function, which will be described below, of this embodiment.

Acoustic Transmission Medium 124

Because a propagation path for photoacoustic waves are provided between the subject 101 and the retaining unit 121, an acoustic transmission medium 124 such as water, an ultrasonic measurement gel or gel sheet may be provided therein to prevent occurrence of an air gap.

Because a propagation path for photoacoustic waves are also provided between the retaining unit 121 and the base material 123 for the subject 101, a medium having a high propagation efficiency for acoustic waves may be filled therein. Because the propagation path also propagates the light 131, a transparent medium such as water may be used for the light 131, for example.

The acoustic transmission medium 124 provided between the subject 101 and the retaining unit 121 and the acoustic transmission medium 124 between the retaining unit 121 and the base material 123 may contain different materials from each other.

Example of Storage Control

The photoacoustic apparatus according to this embodiment allows reduction of the data amount of reception signals output from the acoustic wave receiving elements 211 provided on the base material 123 in a case where a position (or the curvature center point 301) where the directional axes of the plurality of acoustic wave receiving elements 211 are gathered most is not included in a region of interest region of interest. This embodiment may further allow reduction of the data amount of reception signals output from the acoustic wave receiving elements 211 provided on the base material 123 in a case where the high sensitivity region 302 is not included in a region of interest region of interest.

Figure 4A:
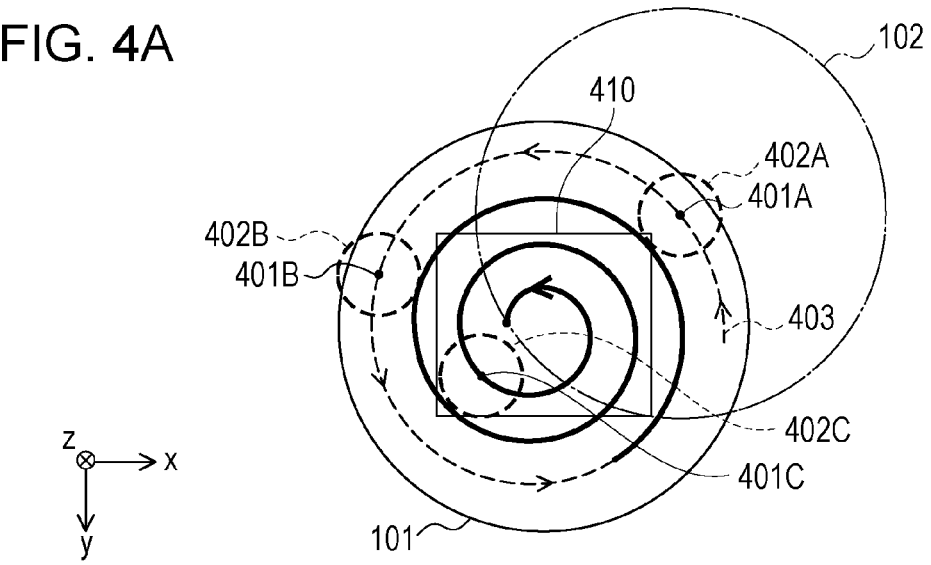
FIGS. 4A to 4C are conceptual diagrams illustrating storage control according to an embodiment.

An example of storage control of reception signals at time points when the subject 101 is irradiated with light will be described below with reference to FIGS. 4A to 4C in a case where the probe 102 is moved according to this embodiment. FIG. 4A is a top view of the probe 102 and subject 101 in a z-axis direction, and FIG. 4B is a side view of the probe 102 and subject 101 in a y-axis direction.

FIG. 4A illustrates a region of interest region of interest region of interest 410 defined as a rectangular parallelepiped shape. The region of interest region of interest has a rectangular parallelepiped for convenience of description, but the application of the present invention is not limited thereto. The present invention is also applicable to cases where the region of interest region of interest has a spherical shape, a hemispherical shape, or other polyhedral shapes.

Figure 4B:
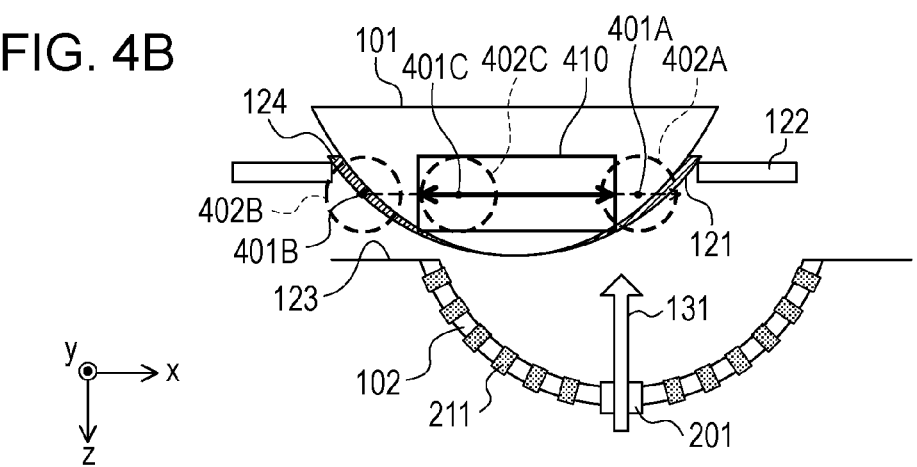
Figure 4C:
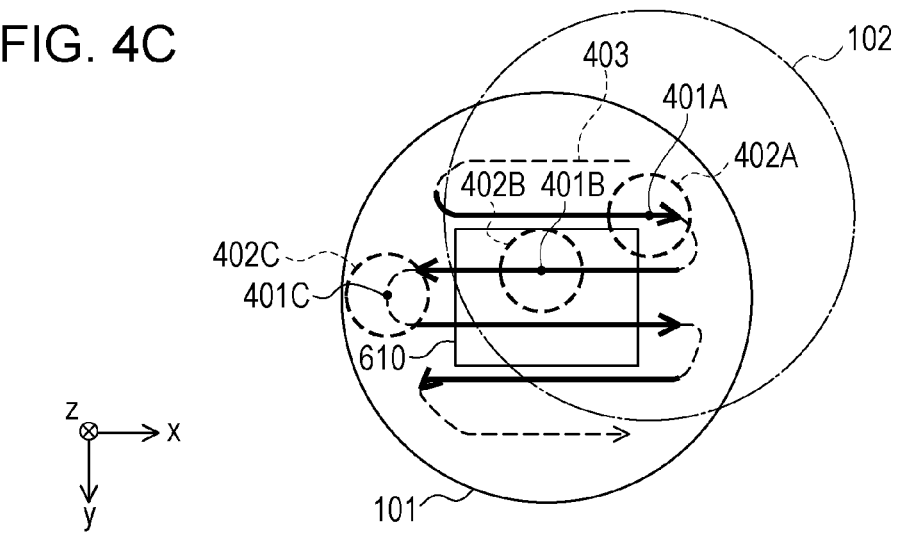

FIGS. 4A and 4C illustrate an example movement path 403 of the probe 102 which renders a spiral with a broken line and a thick solid line.

FIGS. 4A to 4C illustrate curvature center points 401A to 401C of the probe 102 at time points when light is irradiated. FIGS. 4A to 4C illustrate high sensitivity regions 402A to 402C at time points when light is irradiated.

By moving the probe 102 along the moving path 403, the curvature center point 401 and high sensitivity region 402 defined by the probe 102 also move along the moving path 403.

As described above, because a propagation path for the light 131 and photoacoustic waves are provided between the retaining unit 121 and the base material 123, a fluid such as water which is a transparent medium having a high propagation efficiency for photoacoustic waves for the light 131 is used as a medium for propagating acoustic waves. By moving the probe 102 along the spiral moving path 403 constructed by a smooth curved line, the acceleration for moving the probe 102 may be dispersed. Thus, the acceleration applied to the fluid may be reduced as much as possible. Reducing the acceleration applied to the fluid as much as possible may inhibit occurrence of an inhibitory factor against photoacoustic wave propagation such as bubbles caused as a result of collision between the fluid and an apparatus component. Thus, subject information may be acquired with high accuracy.

The control processor 109 calculates whether reception signals output from the probe 102 are to be stored or not when the curvature center of the probe 102 is at the curvature center points 401A to 401C and generates storage control information describing whether the signals are to be stored or not. How it is determined whether signals are to be stored or not will be described below.

When the curvature center of the probe 102 is at the position of at the curvature center point 401B shown in FIG. 4A, the curvature center point 401B and the high sensitivity region 402B do not fall within the region of interest region of interest region of interest 410. Therefore, it is difficult for the acoustic wave receiving elements 211 provided in the probe 102 to receive with high sensitivity photoacoustic waves occurring within the region of interest region of interest region of interest 410. In other words, reception signals output from the acoustic wave receiving elements 211 when the probe 102 is present at the above mentioned position are reception signals which does not largely contribute to highly accurate acquisition of subject information within the region of interest region of interest. Thus, the control processor 109 generates the storage control information to prevent storage of reception signals output from the acoustic wave receiving elements 211 when the probe 102 is present at the above position from being stored in the storage unit 114.

On the other hand, when the curvature center of the probe 102 is at the position of at the curvature center point 401C shown in FIG. 4A, the curvature center point 401C and the high sensitivity region 402C fall within the region of interest region of interest region of interest 410. Thus, the acoustic wave receiving elements provided in the probe 102 receive photoacoustic waves occurring within the region of interest region of interest region of interest 410 with high sensitivity. In other words, reception signals output from the acoustic wave receiving elements 211 when the probe 102 is present at the above mentioned position are reception signals which largely contributes to highly accurate acquisition of subject information within the region of interest region of interest. Thus, the control processor 109 generates the storage control information to allow storage of reception signals output from the acoustic wave receiving elements 211 when the probe 102 is present at the above position from being stored in the storage unit 114.

When the curvature center of the probe 102 is at the position of at the curvature center point 401A in FIG. 4A, the high sensitivity region 402A overlaps with the region of interest region of interest 410. Thus, the control processor 109 is allowed to generate storage control information to allow storage of reception signals output from the acoustic wave receiving elements 211. On the other hand, the curvature center point 401A does not fall within the region of interest region of interest 410, and so reception signals of photoacoustic waves occurring in a region having a highest receiving sensitivity are reception signals occurring in an area excluding the region of interest region of interest 410. Accordingly, when the probe 102 is present at such a position, the control processor 109 may generate storage control information which prevents storage of reception signals output from the acoustic wave receiving elements 211. This may further reduce the data amount of reception signal data stored in the storage unit 114.

The control processor 109 determines whether reception signals are to be stored or not also when the probe 102 is present at a position excluding the positions illustrated in FIGS. 4A to 4C and thus may generate the storage control information.

For simplicity, storage control is illustrated based on two-dimensional (XY-plane) movement of a probe in FIGS. 4A to 4C, but the application of the present invention is not limited thereto. The present invention is also applicable to three-dimensional (within an XYZ-space) movement of the probe 102. Having described above the example in which the probe is moved along a spiral moving path, the moving path applicable in the present invention is not limited thereto. For example, as illustrated in FIG. 4C, in a case where the probe 102 is moved straight, whether reception signals are to be stored or not may be determined based on a result of determination of whether a region where directional axes are gathered falls within a region of interest region of interest or not. In other words, also in the case illustrated in FIG. 4C, whether reception signals are to be stored or not may also be determined based on a positional relationship between the curvature center points 401A to 401C, or the high sensitivity regions 402A to 402C and the region of interest region of interest 410. In FIGS. 4A and 4C the thick solid line of the movement path 403 illustrates when at least the high sensitivity regions 402A to 402C fall within, or overlap with, the region of interest 410.

Flow for Acquiring Subject Information

Next, a flow for acquiring subject information according to this embodiment will be described with reference to the flowchart in FIG. 5.

In step 501, the control processor 109 as a setting unit sets a region of interest region of interest.

For example, the input unit 111 may be used by a user to input a region, and the control processor 109 may set the region as a region of interest region of interest based on information on the region from the input unit 111.

The storage unit 114 may prestore information on a plurality of regions of interest, and a user may use the input unit 111 to select one region of interest from the plurality of regions of interest stored in the storage unit 114. In this case, the control processor 109 may set the region of interest as a region of interest based on information on the arbitrary region of interest from the input unit 111.

The control processor 109 may set a region along a surface of the subject 101 as a region of interest. For example, the control processor 109 may extract a surface of the subject 101 from an image of the subject 101 captured by the image capturing device and set a region along the extracted surface of the subject 101 as a region of interest.

The control processor 109 may read out a region of interest prestored in the storage unit 114 and set it as a region of interest. For example, because the shape of the retaining unit 121 for the subject 101 is known in advance, a region along a surface of the retaining unit 121 may be prestored in the storage unit 114 as a region of interest.

Any region may be set by any method, without being limiting to those described above.

In step 502, the control processor 109 sets a light emission timing, a light irradiation position, and a photoacoustic-wave reception position. In other words, the control processor 109 sets positions of the base material 123 when the subject 101 is irradiated with light from the light source 105 at a plurality of time points, and outputs control information regarding the set positions of the base material 123 to the position control mechanism 104, light source 105, and signal receiving unit 107. According to this embodiment, the base material 123 has an irradiation port 201 at its bottom face, and the irradiation port 201 moves in synchronism with the movement of the base material 123. Thus, setting a position of the base material 123 also sets a light irradiation position and a photoacoustic-wave reception position.

In accordance with a measurement parameter designated by a user by using the input unit 111, the control processor 109 may set measurement conditions such as a light emission timing, a light irradiation position, and a photoacoustic-wave reception position. For example, a measurement parameter which may be designated by a user may be a moving path of the probe 102, and a moving speed, a measurement density, or the number of times of irradiation of the light 131.

For example, a plurality of patterns of positions of the probe 102 at time points when the subject 101 is irradiated with light may be stored in the storage unit 114. In this case, a user may use the input unit 111 to select a pattern from a plurality of patterns. Then, the control processor 109 may set positions of the probe 102 at time points when the subject 101 is irradiated with light based on the information on the pattern output from the input unit 111.

In step 503, the control processor 109 determines whether reception signals are to be stored or not based on the region of interest set in step 501 and the position control information on the probe 102 generated in step 502. In other words, the control processor 109 determines whether reception signals output from the probe 102 at the time points when the subject 101 is irradiated with light in step 507, which will be described below, are to be stored based on the set region of interest and position control information of the probe 102. Then, the control processor 109 generates storage control information describing whether the reception signals are to be stored or not.

In step 504, the position control mechanism 104 moves the position of the probe 102 to the next position for acquiring a next photoacoustic wave signal in accordance with the position control information generated in step 502.

In step 505, the light source 105 emits pulsed light in accordance with a light emission start instruction based on the position control information generated in step 502 from the control processor 109. The pulsed light emitted from the light source 105 is formed into the light 131 through the irradiation optical system 106 and is irradiated to the subject 101.

In step 506, the irradiation optical system 106 generates and outputs a synchronism signal simultaneously with irradiation of the light 131 to the subject 101. The position control mechanism 104 having received the synchronism signal outputs positional information on the probe 102 when the synchronism signal is received to the control processor 109. In other words, the control processor 109 acquires information on coordinates where the probe 102 actually positions when light is irradiated.

In step 507, the control processor 109 determines whether reception signals output from the probe 102 in step 508, which will be described below, are to be stored or not based on the storage control information generated in step 503. If the signals are to be stored, the processing moves to step 508. If not, the processing moves to step 511.

For example, because the position of the probe 102 at light irradiation time points may be deducted in advance from the position control information set in step 502, whether reception signals output at the light irradiation time points are to be stored or not may be predetermined. Thus, the control processor 109 in step 507 may read out from the storage control information the information describing whether signals corresponding to the time point when light is irradiated are to be stored in step 506 or not. The control processor 109 in step 507 may determine whether reception signals output from the probe 102 are to be stored in step 508 or not based on the read storage control information.

The control processor 109 in step 507 may read out from the storage control information the information describing whether signals corresponding to the positional information of the probe 102 acquired in step 506 are to be stored or not. The control processor 109 in step 507 may determine whether reception signals output from the probe 102 are to be stored in step 508 or not based on the read storage control information. According to this method, the information describing whether signals corresponding to the coordinates where the probe 102 actually positions when light is irradiated are to be stored or not may be read out from the storage control information. Thus, even when the position of the probe 102 set in step 502 is displaced from an actual position due to a positioning error caused by the position control mechanism 104 or a light emission jitter from the light source 105, whether the reception signals are to be stored or not may be determined based on the actual position. Therefore, reception signals of photoacoustic waves occurring within a region of interest may be stored selectively with high accuracy. However, in this case, reception signals that are to be stored must be determined not only with respect to the position of the probe 102 set in step 502 but also with another position of the probe 102, and storage control information must be determined based on the determination result in step 503.

The control processor 109 in step 507 may calculate whether reception signals output from the probe 102 in step 508 are to be stored or not based on the region of interest stored in step 501 and positional information on the probe 102 acquired in step 506. Also in this case, because whether the storage is to be performed or not may be determined based on the actual position, reception signals of photoacoustic waves occurring within the region of interest may be selectively stored with high accuracy. When this method is used to determine whether the storage is to be performed or not, the process for generating the storage control information in step 503 may be omitted. Because whether the storage is to be performed or not must be calculated during a period from irradiation of light to output of reception signals from the probe 102, the control processor 109 may require a high processivity. However, even when the control processor 109 has a low processivity, the storage unit 114 having a plurality of computer readable storage media may allow completion of the calculation for determining whether the storage is to be performed or not, while reception signal data are being stored in a computer readable storage medium in a preceding stage. The reception signals determined not to be stored may be deleted without transferring to a computer readable storage medium in a subsequent stage. Also in this case, the data amount of reception signal data to be stored in a computer readable storage medium in the last stage of the storage unit 114 may be reduced.

In step 508, photoacoustic waves caused as a result of irradiation of the light 131 to the subject 101 in step 505 are received by the probe 102 which then outputs reception signals.

In step 509, the signal receiving unit 107 starts sampling the reception signals in synchronism with a synchronism signal input from the irradiation optical system 106 and converts the sampled signals to digital signals. The signal receiving unit 107 having received the synchronism signal, samples a predetermined sample number of reception signals at a predetermined sampling rate. The sample number is determined in view of a velocity of propagation of photoacoustic waves within a subject and a maximum measurement depth as an apparatus specification. The signal receiving unit 107 may perform a process for correcting sensitivity variations between acoustic wave receiving elements on the reception signals output from the probe 102, and a process for complementing a physically or electrically lost acoustic wave receiving element.

In step 510, the reception signals having undergone a signal process performed by the signal receiving unit 107 in step 509 are stored in the storage unit 114 as reception signal data in association with positional information of the probe 102.

The term "reception signal data" herein refers to immediately preceding time-series signal data to be used for acquiring subject information by the image configuration unit 112 in step 511, which will be described below. In other words, it refers to time-series signal data to be stored in a storage unit in the last stage of the storage unit 114 included in the signal data acquisition unit. Thus, this embodiment may only require reduction of the amount of data to be stored in a storage unit in the last stage of the storage unit 114 included in the signal data acquisition unit.

For example, the amount of data to be stored in a storage unit in the last stage may be reduced by reducing the data amount of reception signals corresponding to a data amount reduction period while the signals are being transferred from a storage unit in a preceding stage to a storage unit in a subsequent stage, without reducing the data amount when the signals are stored in a storage unit in the first stage.

In order to reduce the memory capacity of each storage unit of the storage unit 114 included in the signal data acquisition unit, the data amount to be stored in a storage unit in a preceding stage may be reduced. Particularly, the data amount to be stored in a storage unit in the first stage of the storage unit 114 included in the signal data acquisition unit may be reduced. Because such reduction of the data amount in a storage unit in a preceding stage may reduce the data amount to be transferred to a storage unit in subsequent stages, the time period for transferring data may be reduced. Having described that the reception signals not to be stored do not undergo a signal process according to this embodiment, this may not necessarily be the case and the reception signals not to be stored can undergo signal processing as long as such reception signal data is not stored in the storage unit 114. In other words, after performing a signal process on reception signals not to be stored, the reception signals may not be written to the storage unit 114 to avoid storing the signals.

In step 511, the image configuration unit 112 acquires subject information at each target position within the region of interest based on the reception signal data stored in the storage unit 114 in step 510. The image configuration unit 112 may use positional information on the probe 102 when reception signal data are acquired for acquiring subject information to acquire subject information at each target position within the region of interest.

Because an image reconstruction process generally takes time and the process may be committed to a GPU, subject information may be generated in parallel with the operation for acquiring reception signal data. In a case where the image reconstruction process is late for a repetition period of acquisition of reception signal data, successively acquired reception signal data may be managed in a queue so that the image configuration unit 112 may sequential acquire subject information based on reception signal data added to the queue.

In step 512, the image configuration unit 112 adds subject information at each target position within the region of interest generated in step 511 to a voxel value in consideration of the position on volume data of the subject information to be generated. This process may synthesize a plurality of subject information pieces generated from reception signal data a plurality of times. This increases the S/N ratio of the finally acquired subject information.

In step 513, whether all measurements required for generating subject information set in step 502 have completed or not is determined. If not, the processing moves to step 504 where the acquisition of reception signal data is repeated. If yes, the processing moves to step 514.

According to this embodiment, a subject information piece is acquired for each light irradiation, and a plurality of subject information pieces are synthesized to acquire final subject information. Any method may be applied to acquire subject information as long as all acquired reception signal data are used to acquire proper subject information. For example, without performing the processes in step 511 and step 512, all reception signal data are used to perform one image reconstruction process after step 513 so that subject information may be acquired.

For reconstruction of target positions by using reception signal data stored in the storage unit 114 in photoacoustic imaging, reception signal data to be used for the reconstruction may be selected from the following viewpoints.

The reconstruction may use reception signals output by an acoustic wave receiving element 211 having its directional axis passing a target position as described above. This allows reception of acoustic waves occurring at the target position with high sensitivity and may thus increase the S/N ratio of reception signals corresponding to the acoustic waves occurring at the target position. It may therefore increase the S/N ratio of the image intensity at the target position which is reconstructed by using the reception signals.

In a case where a sound source is present at a target position, acoustic waves propagate isotropically from the target position in all directions. Accordingly, reception signal data corresponding to many frequency components of acoustic waves occurring from the target position may be used for the reconstruction. Thus, because energy corresponding to a reconstruction artifact dispersed to all over a reconstructed image during reconstruction processing, local occurrence of a reconstruction artifact may be inhibited.

The reconstruction may use reception signal data acquired by receiving acoustic waves at a position where a reconstruction artifact occurring around a target position is positioned symmetrically about the target position. In other words, receiving elements may receive acoustic waves at point-symmetric positions about the target position. Thus, a reconstruction artifact also occurs point-symmetrically about the target position. Therefore, energy corresponding to the reconstruction artifact disperses uniformly all over the reconstruction image. As a result, a local reconstruction artifact does not occur easily.

Accordingly, the image configuration unit 112 may reconstruct a target position without using reception signals output from the probe 102 when a region where directional axes are gathered most to a target position is not within a region of interest among reception signal data stored in the storage unit 114. In other words, the reconstruction may be performed without using data of reception signals output when the curvature center of the base material 123 does not fit to a target position. This may increase the contrast between a reconstruction image (signal component) and a reconstruction artifact (noise component) at each target position within the region of interest. Because the storage unit 114 does not store reception signals when the curvature center of the base material 123 does not already fit within a region of interest, reception signal data required for a reconstruction as described above are selectively stored in the storage unit 114. Thus, because the amount of reception signal data unnecessary for the reconstruction is less and there is a low possibility that unnecessary data transfer is performed, the time required for the processing may be reduced.

In step 514, the image configuration unit 112 generates a display image based on the subject information acquired in S512 and displays it on the display unit 113. In other words, the image configuration unit 112 causes the display unit 113 to display the subject information acquired in S512 in a display form required for diagnosis.

Having described a high sensitivity region based on a tendency that image quality decreases isotropically from the curvature center of the base material according to this embodiment, the present invention is applicable to high sensitivity regions based on different tendencies. In a case where acoustic wave receiving elements may not be disposed without any gaps therebetween, a high sensitivity region is not a sphere having at its center a position where a plurality of directional axes of the acoustic wave receiving elements are gathered. In this case, a region closer to the base material than a region away from the base material tends to have a higher image quality, with respect to the position where the directional axes of a plurality of acoustic wave receiving elements are gathered at a point. In other words, in this case, a high sensitivity region tends to spread from a region away from the base material to a region close to the base material with respect to the position where the directional axes of a plurality of acoustic wave receiving elements are gathered at a point. A high sensitivity region defined based on this tendency is also applicable to the present invention. In other words, the size of the high sensitivity region may be isotropically from a position where the directional axes of a plurality of acoustic wave receiving elements are gathered at a point.

A predetermined region with reference to the position of the base material may be a high sensitivity region. For example, a high sensitivity region may be a region of a sphere, a cylinder, a quadrangular prism and so on, which is supported by the base material, about a position where the directional axes of a plurality of acoustic wave receiving elements are gathered at a point. As described above, in a case where a high sensitivity region spreads toward the base material, the center of the high sensitivity region is offset closely to the base material from a position where the directional axes of a plurality of acoustic wave receiving elements are gathered at a point. Parameters such as a shape, a size, and a position for defining a high sensitivity region may be preset. Alternatively, in order to define a high sensitivity region, a user may input parameters such as the size and shape of the high sensitivity region by using an input unit.

Having described according to this embodiment that reception signals output when a region where directional axes are gathered does not overlap a region of interest are not stored, the present invention is not limited to the form as long as the data amount may be reduced. For example, the signal receiving unit 107 may sample reception signals by lowering the sampling frequency, for reception signals output when a region where directional axes are gathered does not overlap a region of interest, than the sampling frequency for reception signals output when a region where directional axes are gathered overlaps the region of interest. This may reduce the data amount of reception signals output when a region where directional axes do not overlap a region of interest. Furthermore, because reception signal data of photoacoustic waves occurring in a region excluding a region of interest may be stored, the image of the region excluding the region of interest may be reproduced even with low image quality.

Second Embodiment

A second embodiment will be described with reference to the photoacoustic apparatus illustrated in FIG. 1.

A storage unit 114 as a computer readable storage medium (or recording medium), which stores software program code for implementing functions of the aforementioned embodiment, is supplied to a system or an apparatus. A control processor 109 as a computer (or CPU or MPU) of the system or apparatus reads out and executes the program code stored in the computer readable storage medium. In this case, the program code read out from the computer readable storage medium implements functions of the aforementioned embodiment. The computer readable storage medium storing the program code is included in the present invention.

The computer executes the read program code so that an operating system (OS) running on the computer may perform a part or all of actual processes based on instructs from the program code. A case is also included where the processes implement functions of the aforementioned embodiment.

It is assumed that program code read out from a computer readable storage medium is written to a memory included in a function extension card inserted to the computer or a function extension unit connected to the computer. A case is also included where a CPU included in the function extension card or function extension unit then executes a part or all of actual processes in response to instructions from the program code so that the processes implement functions of the aforementioned embodiment.

When the present invention is applied to the computer readable storage medium, the computer readable storage medium stores program code corresponding to the aforementioned flowchart.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to embodiments, it is to be understood that the invention is not limited to the disclosed embodiments. The scope of the following claims is to be accorded the broadest interpretation so as to encompass all such modifications and equivalent structures and functions.

This application claims the benefit of Japanese Patent Application No. 2014-100849, filed May 14, 2014, which is hereby incorporated by reference herein in its entirety.

What is claimed is:
1. A photoacoustic apparatus comprising:
a light source;
a plurality of receiving elements which receive photoacoustic waves caused by irradiation of light from the light source to a subject and output reception signals;

a base material which supports the plurality of receiving elements such that the directional axes of the plurality of receiving elements are gathered at a point;

a control unit which determines a position of the base material at each of a plurality of time points when light from the light source is irradiated to the subject;

a moving mechanism which moves the base material to the position of the base material determined by the control unit;

a signal data acquisition unit which generates and stores reception signal data based on the reception signal output from the plurality of receiving elements;

a setting unit which sets a region of interest; and an information acquisition unit which acquires subject information in the region of interest based on the reception signal data stored in the signal data acquisition unit, wherein the signal data acquisition unit generates and stores the reception signal data by reducing a data amount of the reception signals output from the plurality of receiving elements if a region where the directional axes of the plurality of receiving elements are gathered at a point is not included in the region of interest.

2. The photoacoustic apparatus according to claim 1, wherein
the signal data acquisition unit does not store the reception signals output from the plurality of receiving elements when the region where the directional axes of the plurality of receiving elements are gathered at a point is not included in the region of interest.

3. The photoacoustic apparatus according to claim 1, wherein
the signal data acquisition unit generates and stores the reception signal data by lowering a sampling frequency for the reception signal output from the plurality of receiving elements when the region where the directional axes of the plurality of receiving elements are gathered at a point is not included in the region of interest, as compared to a sampling frequency for the reception signal output from the plurality of receiving elements when the region where the directional axes of the plurality of receiving elements are gathered at a point is included in the region of interest.

4. The photoacoustic apparatus according to claim 1, wherein
for a target position within the region of interest, the information acquisition unit acquires the subject information at the target position within the region of interest without using reception signal data, among the reception signal data stored in the signal data acquisition unit, corresponding to reception signals output from the plurality of receiving elements, when the region where the directional axes of the plurality of receiving elements are gathered at a point is not included in the target position.

5. The photoacoustic apparatus according to claim 1, wherein the signal data acquisition unit generates and stores the reception signal data by reducing the data amount of the reception signals output from the plurality of receiving elements when a high sensitivity region where each of the plurality of receiving elements are capable of receiving photoacoustic waves with high sensitivity is not included in the region of interest.

6. The photoacoustic apparatus according to claim 1, further comprising an input unit by which a region may be input, wherein
the setting unit sets the arbitrary region as the region of interest based on information on the arbitrary region output from the input unit.

7. The photoacoustic apparatus according to claim 1, further comprising:
a storage unit which stores information on a plurality of regions of interest; and
an input unit by which an arbitrary region of interest may be selected from the plurality of regions of interest, wherein the setting unit sets the arbitrary region of interest as the region of interest based on information on the arbitrary region of interest output from the input unit.

8. The photoacoustic apparatus according to claim 1, further comprising:
a storage unit which stores information on a plurality of patterns of a position of the base material; and
an input unit by which a pattern may be selected from the plurality of patterns, wherein
the control unit sets a position of the base material corresponding to the pattern based on information on the pattern output from the input unit.

9. The photoacoustic apparatus according to claim 1, wherein
the control unit
acquires positional information on the base material when light from the light source is irradiated to the subject; and
generates control information describing whether the data amount of the reception signals output from the plurality of receiving elements is to be reduced based on the region of interest set by the setting unit and the positional information on the base material when light from the light source is irradiated to the subject; and
the signal data acquisition unit generates and stores the reception signal data by reducing the data amount of the reception signals output from the plurality of receiving elements based on the control information generated by the control unit.

10. The photoacoustic apparatus according to claim 1, wherein
the control unit
generates control information describing whether the data amount of the reception signals output from the plurality of receiving elements is to be reduced or not based on the region of interest set by the setting unit and a position of the base material set by the control unit;
acquires positional information of the base material when light from the light source is irradiated to the subject; and
selects control information corresponding to the positional information of the base material from the control information; and
the signal data acquisition unit generates and stores the reception signal data by reducing the data amount of the reception signals output from the plurality of receiving elements based on the selected control information.

11. A photoacoustic apparatus comprising:
a light source;
a plurality of receiving elements which receive photoacoustic waves caused by irradiation of light from the light source to a subject and output reception signals;
a base material which supports the plurality of receiving elements on a curved surface based on a spherical;

a control unit which determines a position of the base material at each of a plurality of time points when light from the light source is irradiated to the subject;

a moving mechanism which moves the base material to the position of the base material determined by the control unit;

a signal data acquisition unit which generates and stores reception signal data based on the reception signal output from the plurality of receiving elements;

a setting unit which sets a region of interest; and an information acquisition unit which acquires subject information in the region of interest based on the reception signal data stored in the signal data acquisition unit, wherein the signal data acquisition unit generates and stores the reception signal data by reducing a data amount of the reception signals output from the plurality of receiving elements if a region where the curvature center of the base material is not included in the region of interest.

12. The photoacoustic apparatus according to claim 11, wherein
the signal data acquisition unit does not store the reception signals output from the plurality of receiving elements when the curvature center of the base material is not included in the region of interest.

13. The photoacoustic apparatus according to claim 11, wherein
the signal data acquisition unit generates and stores the reception signal data by lowering a sampling frequency for the reception signal output from the plurality of receiving elements when the curvature center of the base material is not included in the region of interest, as compared to a sampling frequency for the reception signal output from the plurality of receiving elements when the curvature center of the base material is included in the region of interest.

14. The photoacoustic apparatus according to claim 11, wherein
for a target position within the region of interest, the information acquisition unit acquires the subject information at the target position within the region of interest without using reception signal data, among the reception signal data stored in the signal data acquisition unit, corresponding to reception signals output from the plurality of receiving elements when the curvature center of the base material is not included in the target position.

15. The photoacoustic apparatus according to claim 11, wherein
the signal data acquisition unit generates and stores the reception signal data by reducing the data amount of the reception signals output from the plurality of receiving elements when a high sensitivity region where each of the plurality of receiving elements are capable of receiving photoacoustic waves with high sensitivity is not included in the region of interest.

16. The photoacoustic apparatus according to claim 11, further comprising an input unit by which a region may be input, wherein
the setting unit sets the arbitrary region as the region of interest based on information on the arbitrary region output from the input unit.

17. The photoacoustic apparatus according to claim 11, further comprising:
a storage unit which stores information on a plurality of regions of interest; and
an input unit by which a region of interest may be selected from the plurality of regions of interest,
wherein the setting unit sets the selected region of interest as the region of interest based on information on the region of interest selected from the input unit.

18. The photoacoustic apparatus according to claim 11, further comprising:
a storage unit which stores information on a plurality of patterns of a position of the base material; and
an input unit by which a pattern may be selected from the plurality of patterns, wherein
the control unit sets a position of the base material corresponding to the selected pattern based on information on the pattern selected from the input unit.

19. The photoacoustic apparatus according to claim 11, wherein
the control unit:
acquires positional information on the base material when light from the light source is irradiated to the subject; and
generates control information describing whether the data amount of the reception signals output from the plurality of receiving elements is to be reduced based on the region of interest set by the setting unit and the positional information on the base material when light from the light source is irradiated to the subject; and
the signal data acquisition unit generates and stores the reception signal data by reducing the data amount of the reception signals output from the plurality of receiving elements based on the control information generated by the control unit.

20. The photoacoustic apparatus according to claim 11, wherein
the control unit:
generates control information describing whether the data amount of the reception signals output from the plurality of receiving elements is to be reduced or not based on the region of interest set by the setting unit and a position of the base material set by the control unit;
acquires positional information of the base material when light from the light source is irradiated to the subject; and
selects control information corresponding to the positional information of the base material from the control information; and
the signal data acquisition unit generates and stores the reception signal data by reducing the data amount of the reception signals output from the plurality of receiving elements based on the selected control information.

* * * * *